(12) United States Patent
Denmeade et al.

(10) Patent No.: US 8,957,016 B2
(45) Date of Patent: Feb. 17, 2015

(54) TUMOR ACTIVATED PRODRUGS

(75) Inventors: Samuel R. Denmeade, Ellicot City, MD (US); John T. Isaacs, Phoenix, MD (US)

(73) Assignee: Genspera, Inc.

( * ) Notice: Subject to any disclaimer, the term of this patent is extended or adjusted under 35 U.S.C. 154(b) by 108 days.

(21) Appl. No.: 13/485,595

(22) Filed: May 31, 2012

(65) Prior Publication Data

US 2012/0270768 A1     Oct. 25, 2012

Related U.S. Application Data

(62) Division of application No. 12/613,357, filed on Nov. 5, 2009, now abandoned, which is a division of application No. 11/328,491, filed on Jan. 6, 2006, now Pat. No. 7,635,682.

(51) Int. Cl.
| | |
|---|---|
| *A61K 38/08* | (2006.01) |
| *C07K 7/06* | (2006.01) |
| *A61K 38/16* | (2006.01) |
| *A61K 47/48* | (2006.01) |

(52) U.S. Cl.
CPC .............. *A61K 38/08* (2013.01); *A61K 38/168* (2013.01); *A61K 47/48338* (2013.01); *C07K 7/06* (2013.01)
USPC .............................. 514/1.3; 530/322; 530/329

(58) Field of Classification Search
None
See application file for complete search history.

(56) References Cited

FOREIGN PATENT DOCUMENTS

WO    WO 98/52966    * 5/1998

OTHER PUBLICATIONS

Pinto, The Prostate Journal, 1999, vol. 1, pp. 15-26.*
Denmeade, Enzymatic Activation of Proteasome Inhibitor Prodrugs by PSA as Targeted Therapy for Prostate Cancer, 2001, pp. 1-15.*

* cited by examiner

*Primary Examiner* — Karlheinz R Skowronek
*Assistant Examiner* — Roy Teller
(74) *Attorney, Agent, or Firm* — Holly Logue; Logue PC

(57) ABSTRACT

The instant invention provides compositions comprising a prodrug, the prodrug comprising a therapeutically active drug; and a peptide selected from the group consisting of the sequences: Ser-Ser-Lys-Tyr-Gln (SEQ ID NO:1); Gly-Lys-Ser-Gln-Tyr-Gln (SEQ ID NO:2); and Gly-Ser-Ala-Lys-Tyr-Gln (SEQ ID NO:3) wherein the peptide is linked to the therapeutically active drug to inhibit the therapeutic activity of the drug, and wherein the therapeutically active drug is cleaved from the peptide upon proteolysis by an enzyme having a proteolytic activity of prostate specific antigen (PSA). The invention further provides methods of making and using the claimed compositions.

31 Claims, 4 Drawing Sheets

TUMOR ACTIVATED PRODRUGS

CROSS REFERENCE TO RELATED APPLICATIONS

This application is a divisional application of U.S. application Ser. No. 12/613,357, filed on Nov. 5, 2009 (abandoned), which is a divisional application of U.S. application Ser. No. 11/328,491, filed on Jan. 6, 2006, now U.S. Pat. No. 7,635,682, each of which is hereby incorporated by reference in their entireties.

GOVERNMENT FUNDING

This invention was made, in whole or in part, by grant P50CA58236 from the National Cancer Institute. Accordingly, the Government may have certain rights in the invention.

SEQUENCE LISTING

The instant application contains a Sequence Listing which has been submitted in ASCII format via EFS-Web and is hereby incorporated by reference in its entirety. Said ASCII copy, created on Sep. 30, 2013, is named GENS.0029_SL.txt and is 11,393 bytes in size.

FIELD OF THE INVENTION

This invention relates generally to the targeted activation of biologically active materials to cells that produce prostate specific antigen (PSA) and more specifically to PSA-cleavable peptides that activate therapeutic drugs.

BACKGROUND OF THE INVENTION

There is currently no effective therapy for men with metastatic prostate cancer who relapse after androgen ablation, even though numerous agents have been tested over the past thirty years. Prolonged administration of effective concentrations of standard chemotherapeutic agents is usually not possible because of dose-limiting systemic toxicities.

Prostate specific antigen (PSA) is a 33,000 kDa single chain glycoprotein first characterized from human prostate tissue. PSA is synthesized and secreted as a unique differentiation product of the prostatic glandular cells, both from normal and cancerous cells. Low levels of PSA are detected in normal and cancerous breast tissue also.

Prostate Specific Antigen (PSA) is a chymotrypsin-like serine protease that is measurable in the blood and is used as a clinical test to detect prostate cancer and follow response to therapy. However, PSA is not active in the blood and is only active within tumor sites and in the normal prostate tissue. The concept of capitalizing upon the prostate specific expression of the protease PSA to target therapeutic agents to prostate cancer sites was first proposed in 1992. Since that time, considerable development, research and systematic effort have been applied to bring that idea to fruition. These efforts have resulted in identification of an initial PSA-activated pro-drugs which have been described in detail elsewhere (see, for example, U.S. Pat. No. 6,410,514).

Thapsigargin (TG) is an sesquiterpene-γ-lactone available by extraction from the seeds and roots of the umbelliferous plant *Thapsia garganica* L. Thapsigargin selectively inhibits the sarcoplasmic reticulum (SR) and endoplasmic reticulum (ER) $Ca^{2+}$-ATPase (SERCA) pump, found in skeletal, cardiac, muscle and brain microsomes. The apparent dissociation constant is 2.2 pM or less.

TG operates by what is believed to be a unique method of killing cells. TG induced inhibition of the SERCA pump leads to depletion of the ER $Ca^{2+}$ pool. This depletion apparently results in the generation of a signal, possibly from an ER-derived diffusible messenger, so that the plasma membrane is more permeable to extracellular divalent cations. The resulting influx of these cations is responsible for the death of cells.

TG is poorly soluble in water, does not possess cell specificity, and is able to kill quiescent $G_o$ cells. For these reasons, unmodified TG would be difficult to administer and deliver systemically without significant non-specific host toxicity.

Accordingly, the need exists for improved tumor-activated pro-drugs for the treatment of cell proliferative disorders, e.g., cancer.

SUMMARY OF THE INVENTION

The present invention provides peptides consisting of or comprising SSKYQ (SEQ ID NO: 1) that include a cleavage site for prostate specific antigen (PSA) and other enzymes with the same activity and proteolytic specificity as PSA. The invention also provides analogs, derivatives and conservative variations of these peptides.

The invention also provides a therapeutic prodrug composition, comprising a therapeutic drug linked to a peptide of the invention which is specifically cleaved by PSA. The linkage substantially inhibits the non-specific toxicity of the drug, and cleavage of the peptide releases the drug, activating it or restoring its non-specific toxicity. The invention provides therapeutic prodrug compositions comprising a peptide of the invention, e.g., SSKYQ (SEQ ID NO: 1), and a thapsigargin or a thapsigargin derivative. The thapsigargins are a group of natural products isolated from species of the umbelliferous genus *Thapsia*. The term "thapsigargins" has been defined by Christensen, et al., *Prog. Chem. Nat. Prod.*, 71 (1997) 130-165. These derivatives contain a means of linking the therapeutic drug to carrier moieties, including peptides and antibodies. The peptides and antibodies can include those which specifically interact with antigens including PSA. The interactions can involve cleavage of the peptide to release the therapeutic analogs of sesquiterpene-γ-lactones.

Prodrug composition comprising a PSA cleavable peptide and a therapeutic drug have been previously disclosed (see, for example, U.S. Pat. No. 6,410,514). The prodrug compositions disclosed herein have improved characteristics as compared to the compositions previously described. Unexpectedly, the prodrug compositions described herein have increased hydrolysis by PSA, increased antitumor efficacy, and increased generation of therapeutic drug at the site of the tumor as compared to the compositions previously described.

The invention also provides a method for treating cell proliferative disorders, including those which involve the production of PSA, in subjects having, or at risk of having such disorders. The method involves administering to the subject a therapeutically effective amount of the composition of the invention.

The invention also provides a method of producing the prodrug composition of the invention. In another embodiment, the invention provides a method of detecting PSA activity in tissue. In yet another embodiment, the invention provides a method of selecting appropriate prodrugs for use in treating cell proliferative disorders involving PSA production.

The invention also provides a method for detecting a cell proliferative disorder associated with PSA production in a tissue of a subject, comprising contacting a target cellular component suspected of having a PSA associated disorder, with a reagent which detects enzymatically active PSA.

The invention also provides a method of determining PSA activity in a PSA-containing sample, comprising contacting the sample with a detectably labeled peptide of the invention which is specifically cleaved by PSA for a period of time sufficient to allow PSA to cleave the peptide, detecting the detectable label to yield a detection level, which is then compared to the detection level obtained by contacting the same detectably labeled peptide with a standard PSA sample of known activity.

The invention also provides a method of imaging soft tissue and/or bone metastases which produce PSA, comprising administering a lipophilic imaging label linked to a peptide of the invention which is specifically cleaved by PSA to a subject having or suspected of having a PSA-associated cell proliferative disorder, allowing PSA to cleave the peptide, allowing the lipophilic imaging label to accumulate in the tissue and/or bone, allowing the subject to clear the uncleaved peptide, and imaging the subject for diagnostic purposes.

Unless otherwise defined, all technical and scientific terms used herein have the ordinary meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other reference materials mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

FIG. 2 discloses SEQ ID NOS 5 and 4, respectively, in order of appearance.

FIG. 3 discloses SEQ ID NOS 4-5, respectively, in order of appearance.

FIG. 4 discloses SEQ ID NOS 5 and 4, respectively, in order of appearance.

DETAILED DESCRIPTION

Figure 1A:
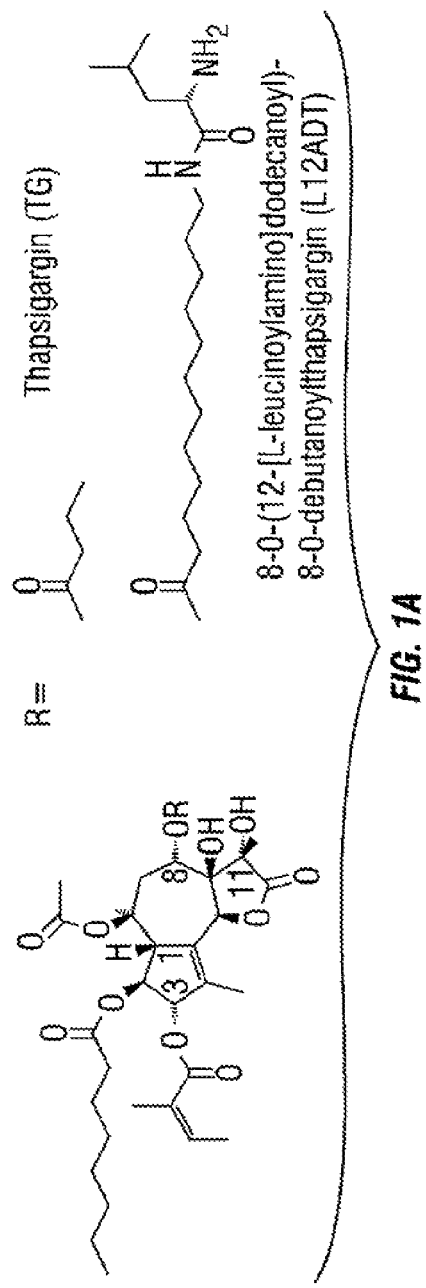
FIG. 1 depicts the chemical structures of (A) Thapsigargin and L12ADT; (B) Mu-HSSKLQ//L12ADT (SEQ ID NO: 4); and (C) Mu-SSKYQ//L12ADT (SEQ ID NO: 5) (the // represents the location of PSA cleavage).

The invention provides novel peptides consisting of or comprising the amino acid sequence Ser-Ser-Lys-Tyr-Gln (SSKYQ) (SEQ ID NO: 1) which contain a cleavage site specific for prostate specific antigen (PSA). In other preferred embodiments of the invention are provided novel peptides consisting of or comprising the amino acid sequence Gly-Lys-Ser-Gln-Tyr-Gln (GKSQYQ) (SEQ ID NO: 2) and Gly-Ser-Ala-Lys-Tyr-Gln (GSAKYQ) (SEQ ID NO: 3). These peptides are efficiently and specifically cleaved by PSA. The peptide is useful for substantially inhibiting the non-specific toxicity of the therapeutic agents prior to the agents contacting a tissue containing PSA. The invention further provides prodrugs comprising sesquiterpene-γ-lactone analogs linked to a peptide of the invention as described herein. The linkage substantially converts the derivative into an inactive prodrug. The compositions do not show significant non-specific toxicity, but in environments where PSA is found, the composition becomes activated when peptide is cleaved, releasing the therapeutic drug, which regains its non-specific toxicity.

PSA-Specific Peptides

As used herein, the term "prostate specific antigen" (PSA) means prostate specific antigen, as well as all other proteases that have the same or substantially the same proteolytic cleavage specificity as prostate specific antigen. As used herein, "sufficiently toxic" refers to therapeutic drugs which display nonspecific toxicity toward cells with an $LC_{50}$ concentration that is at least 3 times lower than the $LC_{50}$ concentration of the prodrugs of the invention, more preferably at least 20 times lower, and therapeutic drugs most preferably have an $LC_{50}$ concentration that is at least 100 times lower than the $LC_{50}$ concentration of the prodrugs of the invention. The term "contacting" refers to exposing tissue to the peptides, therapeutic drugs or prodrugs of the invention so that they can effectively inhibit cellular processes, or kill cells. Contacting may be in vitro, for example by adding the peptide, drug, or prodrug to a tissue culture to test for susceptibility of the tissue to the peptide, drug or prodrug. Contacting may be in vivo, for example administering the peptide, drug or prodrug to a subject with a cell proliferative disorder, such as prostate or breast cancer or benign prostatic hypertrophy. By "polypeptide" is meant any chain of amino acids, regardless of length or post-translational modification (e.g., glycosylation or phosphorylation). As written herein, amino acid sequences are presented according to the standard convention, namely that the amino terminus of the peptide is on the left, and the carboxy terminus on the right. In one aspect, the invention features a peptide, e.g., SSKYQ (SEQ ID NO: 1), that includes a cleavage recognition site for PSA or an enzyme having a proteolytic activity of PSA. The preferred amino acid sequences of the invention is linear.

The cleavage site recognized by PSA is flanked by the amino acid sequences SSKYQ (SEQ ID NO: 1), GKSQYQ (SEQ ID NO: 2), or GSAKYQ (SEQ ID NO: 3). The PSA cleavage site is located at the carboxy terminal side of Q.

Further examples of the peptides of the invention are constructed as analogs of, derivatives of, and conservative variations on the amino acids sequence SSKYQ (SEQ ID NO: 1), GKSQYQ (SEQ ID NO: 2), or GSAKYQ (SEQ ID NO: 3). Thus, the broader group of peptides having hydrophilic and hydrophobic substitutions, and conservative variations are encompassed by the invention. The term "isolated" as used herein refers to a peptide substantially free of proteins, lipids, nucleic acids, for example, with which it is naturally associated. Those of skill in the art can make similar substitutions to achieve peptides with greater activity and/or specificity toward PSA. For example, the invention includes the peptide sequences described above, as well as analogs or derivatives thereof, as long as the bioactivity of the peptide remains. Minor modifications of the primary amino acid sequence of the peptides of the invention may result in peptides which have substantially equivalent activity as compared to the specific peptides described herein. Such modifications may be deliberate, as by site-directed mutagenesis or chemical synthesis, or may be spontaneous. All of the peptides produced by these modifications are included herein, as long as the biological activity of the original peptide remains, i.e., susceptibility to cleavage by PSA.

Peptides of the invention include any analog, homolog, mutant, isomer or derivative of the peptides disclosed in the present invention, as long as the bioactivity as described herein remains. All peptides were synthesized using L-amino acids; however, D-forms of the amino acids can be synthetically produced. In one embodiment, one or two of the serine residues in the peptides of the invention are D-Serine residues.

The peptides of the invention include peptides which are conservative variations of those peptides specifically exemplified herein. The term "conservative variation" as used herein denotes the replacement of an amino acid residue by another, biologically similar residue. Examples of conservative variations include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine, and threonine. The term "conservative variation" also includes the use of a substituted amino acid in place of an unsubstituted parent amino acid provided that antibodies raised to the substituted polypeptide also immunoreact with the unsubstituted polypeptide.

A wide variety of groups can be linked to the carboxy terminus peptides consisting of or comprising SSKYQ (SEQ ID NO: 1), GKSQYQ (SEQ ID NO: 2), or GSAKYQ (SEQ ID NO: 3). Notably, therapeutic drugs can be linked to this position. In this way, advantage is taken of the PSA-specificity of the cleavage site, as well as other functional characteristics of the peptides of the invention. Preferably, the therapeutic drugs are linked to the carboxy terminus either directly or through a linker group. The direct linkage is preferably through an amide bond, in order to utilize the proteolytic activity and specificity of PSA. If the connection between the therapeutic drug and the amino acid sequence is made through a linker, this connection is also preferably made through an amide bond, for the same reason. The linker may be connected to the therapeutic drug through any of the bond types and chemical groups known to those skilled in the art. The linker may remain on the therapeutic drug indefinitely after cleavage, or may be removed soon thereafter, either by further reactions with external agents, or in a self-cleaving step. Self-cleaving linkers are those linkers which can intramolecularly cyclized and release the drug, or undergo spontaneous $S_{N\,1}$ solvolysis and release the drug upon peptide cleavage. Such linkers are for example 2,2-dialkyl-2-(2-anisyl) acetic acid, described in Atwell et al., *J. Med. Chem.*, 37:371-380, (1994), and p-amidobenzyloxycarbonyl, described in Carl et al., *J. Med. Chem.*, 24:479-480, (1981). Further useful examples are provided in these references. Other materials such as detectable labels or imaging compounds can be linked to the peptide. Groups can also be linked to the amino terminus of the peptides described herein, including such moieties as antibodies, and peptide toxins, including the 26 amino acid toxin, melittin and the 35 amino acid toxin, cecropin B, for example. Both of these peptide toxins have shown toxicity against cancer cell lines.

The length of the amino acid sequence plays a role in the ability of PSA to cleave the peptide, with at least a tetrapeptide required for activity. Tetrapeptides as recited above typically are not as soluble as hexapeptides, although PSA cleavage activity is similar. One skilled in the art will be able to readily identify specific groups to improve the water solubility of the peptides of the invention. Among the groups which should be considered are polysaccharides, including dextrans, cyclodextrins, starches and the like, including derivatives thereof. Therapeutic drugs which are water soluble may be linked to the peptides of the invention, thereby imparting water solubility to the complexes as a whole. The peptides of the invention may also contain conventional capping groups connected to the amino terminus of the peptide to prevent endopeptidase activity from degrading the peptide. Such capping groups include acetyl, succinyl, benzyloxycarbonyl, glutaryl, morpholinocarbonyl, and many others known in the art.

Amino acid sequences can be constructed that contain highly specific cleavage sites for PSA. The highly PSA-specific cleavage sites of the invention are cleaved by PSA to yield at least 5 picomoles of cleaved peptide per minute per 200 picomoles of PSA. Preferably, the peptides contain PSA-specific cleavage sites that yield at least 10 picomoles of cleaved peptide per minute per 200 picomoles of PSA. Most preferably, such cleavage sites yield at least 15 picomoles of cleaved peptide per minute per 200 picomoles of PSA.

Amino acid sequences can be constructed that are highly selective towards cleavage by PSA, so that cleavage by other purified extracellular proteases is minimized. Preferably, the peptides of the invention are cleaved by extracellular proteases other than PSA to yield not more than 4.0 picomoles of cleaved peptide per minute per 200 picomoles of purified extracellular non-PSA proteases. More preferably, the peptides are cleaved to yield not more than 2.0 picomoles of cleaved peptide per minute per 200 picomoles of purified extracellular non-PSA enzyme. Most preferably, not more than 2.0 picomole per minute of peptide are cleaved per 200 picomoles of purified extracellular non-PSA enzyme.

Highly PSA-specific amino acid sequences can be constructed that are also stable toward cleavage in sera. Preferably, the peptides containing this sequence yield at most 2.0 picomoles per minute of cleaved peptide in human serum. More preferably, the peptides containing this sequence yield at most 1.75 picomoles per minute of cleaved peptide in human serum. Most preferably, at most 1.5 picomoles per minute of cleaved peptide are yielded by enzymes found in human serum.

The preferred amino acid sequences of the invention is also highly selective towards cleavage by PSA as compared to purified intracellular proteases. Preferably, the peptides of the invention are cleaved by intracellular proteases other than PSA to yield not more than 35 picomoles of cleaved peptide per minute per 200 picomoles of purified intracellular protease. More preferably, the peptide do not yield more than 20 picomoles of cleaved peptide. Most preferably, not more than 5 picomoles of cleaved peptide are produced upon cleavage by purified intracellular proteases other than PSA. While not wishing to be bound by any particular theory, it is believed that essentially no pathogenic effects arise from cleavage of the peptides of the compositions of the invention through intracellular proteases, and that these proteases do not play a significant role in the activation of the therapeutic drugs of the invention.

The peptides of the invention can be synthesized according to any of the recognized procedures in the art, including such commonly used methods as t-bcc or fmoc protection of alpha-amino groups. Both methods involve stepwise syntheses whereby a single amino acid is added at each step starting from the C-terminus of the peptide. (See, Coligan, et al., *Current Protocols in Immunology*, Wiley Interscience, 1991, Unit 9). Peptides of the invention can also be synthesized by the well-known solid phase peptide synthesis methods described in Merrifield, *J. Am. Chem. Soc.*, 85:2149, 1962), and Stewart and Young, *Solid Phase Peptide Synthesis*, (Freeman, San Francisco, 1969, pp. 27-62), using a copoly(styrene-divinylbenzene) containing 0.1-1.0 mM amine/gram polymer. On completion of chemical synthesis, the peptides can be deprotected and cleaved from the polymer by treatment with liquid HF-10% anisole for about ¼ to 1 hour at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as solvent. Lyophilization of appropriate fractions of the column will yield the homogeneous peptide of peptide derivatives, which can then be characterized by such standard techniques as amino acid analysis, thin layer chromatography, high performance liquid chromatography, ultraviolet absorption spectroscopy, molar rotation, solubility, and quantitated by solid phase Edman degradation.

The invention encompasses isolated nucleic acid molecules encoding the peptides of the invention, vectors containing these nucleic acid molecules, cells harboring recombinant DNA encoding the peptides of the invention, and fusion proteins which include the peptides of the invention. Especially preferred are nucleic acid molecules encoding the polypeptides described herein.

Prodrug Compositions

The invention also features prodrug compositions which comprise a therapeutic drug linked to a peptide as described herein, e.g., a peptide containing a cleavage site that is specific for prostate specific antigen or any enzyme which has the enzymatic activity of prostate specific antigen (PSA). As noted above, the peptides of the invention can be used to activate therapeutic drugs at PSA producing tissue. The peptides which are useful in the prodrugs of the invention are those described above.

The therapeutic drugs that may be used in the prodrugs of the invention include any drugs which can be directly or indirectly linked to the PSA-specifically cleavable peptides of the invention. Preferred drugs are those containing primary amines. The presence of a primary amine allows the formation of an amide bond between the drug and the peptide. This bond serves as the cleavage site for PSA. The primary amines may be found in the drugs as commonly provided, or they may be added to the drugs by chemical synthesis. The presence of the primary amine must allow the therapeutic drug to retain its non-specific toxicity when cleaved. Certain therapeutic drugs contain primary amines, for example, anthracycline antibiotics containing an amino sugar such as doxorubicin, daunorubicin, epirubicin (4-epidoxorubicin), idarubicin (4-demethoxydaunomycin) and the like. These drugs intercalate into polynucleotides and interfere with replication processes. Other therapeutic drugs are required to have primary amines introduced by chemical or biochemical synthesis, for example, sesquiterpene-γ-lactones such as those belonging to the guaianolide, inuchineolide, germacranolide, and eudesmanolide families of sesquiterpenoids. These include estafiatin, grossheimin, inuchinenolide, arglabin, thapsigargin and their derivatives, such as thapsigargicin and many others known to those skilled in the art. Thapsigargin and its derivatives are believed to act by inhibiting the SERCA pump found in many cells.

In an alternative embodiment, a peptide of the invention is linked to a polypeptide therapeutic. In a specific example, a peptide of the invention can be linked to, for example, a bacterial toxin, e.g., aerolysin, hemolysin, colicin, or diphtheria toxin. The bacterial toxin would be inactive until the cleavage of the polypeptide by PSA, thereby creating a targeted cancer therapeutic.

The peptide and therapeutic drug are linked directly or indirectly (by a linker) through the carboxy terminus of the terminal amino acid residue. The site of attachment on the therapeutic drug must be such that the non-specific toxicity of the drug is substantially inhibited. Thus, the prodrug should not be significantly toxic. In other words, the $LC_{50}$ concentration of the therapeutic drug should be at least 5 times lower than the $LC_{50}$ concentration of the prodrugs of the invention, more preferably at least 20 times lower, and most preferably the $LC_{50}$ concentration of the therapeutic drug should be at least 100 times lower than the $LC_{50}$ concentration of the prodrugs of the invention.

In certain embodiments, the peptide and drug can be connected indirectly through a linker. The linker can either remain attached to the drug or be cleaved off. In embodiments in which the linker remains attached to the drug, the linker can be any group which does not substantially inhibit the non-specific toxicity of the drug after cleavage from the peptide. Suitable linkers are primary amine containing alkanoyl, alkenoyl, and arenoyl substituents. Examples of such linkers are $CO-(CH=CH)_{n1}-(CH_2)_{n2}-Ar-NH_2$, $CO-(CH_2)_{n2}-(CH=CH)_{n1}-Ar-NH_2$, $CO-(CH)_{n2}-(CH=CH)_{n1}-CO-NH-Ar-NH_2$ and $CO-(CH=CH)_{n1}-(CH_2)_{n2}-CO-NH-Ar-NH_2$ and substituted variations thereof, where n1 and n2 are from 0 to 5, and Ar is any substituted or unsubstituted aryl group. Substituents which may be present on Ar include short and medium chain alkyl, alkanoxy, aryl, aryloxy, and alkenoxy groups, nitro, halo, and primary secondary or tertiary amino groups, as well as such groups connected to Ar by ester or amide linkages. Amino acids can also serve as linkers.

In other embodiments, the linker is self-cleaving. Self-cleaving linkers are those which are disposed to cleave from the drug after the cleavage of the peptide by PSA. The linkers generally contain primary amines which form amide bonds to the carboxy terminus of the peptide sequence. The linkers can also contain a carboxylic acid which forms an amide bond to a primary amine found on the drug.

One method of linker self-cleavage relies on spontaneous $S_{N1}$, solvolysis of the linker, activated by the cleavage of the peptide by PSA. The cleavage of the amide bond between the peptide terminal carboxyl group and the primary amine on the linker releases π electron density into an aromatic system present in the linker, stabilizing the development of a positive charge developing on a carbon atom a to the aromatic system. This charge stabilization eliminates the carboxylic acid, which is subsequently hydrolyzed from the drug. Examples of self-cleaving linkers of this type include p-amidobenzyloxycarbonyl, and substituted derivatives which do not significantly detrimentally affect the stabilization of positive charge at the α carbon.

Another method of linker self-cleavage utilizes cyclization of aromatic amines substituted with alkanone groups which allow the formation of intramolecular cyclic structures utilizing the lone electron pair of the amine which attack an electrophilic carbon such as that of the carbonyl. Five and six membered rings are formed preferably from such cyclization. Useful examples include 2-(2-anisyl)acetic acids and 3-(2-anisyl)propionic acids, as well as acid derivatives. With respect to such derivatives, short chain alkyl groups such as methyl, ethyl are useful as substituents. Naphthalene derivatives such as 8-amino-1-naphthalenecarboxylic acid and 8-amino-1-naphthaleneacetic acid derivatives.

As outlined above, peptide cleavage frees the electrons of the amine, which attack the carbonyl carbon, allowing the drug (leaving group) to be released. The carboxy terminus of the peptide is attached to the primary amine group of the linker by an amide bond, and the primary amine of the drug is attached to the carboxylic acid group of the linker, also by an amide bond.

In such embodiments, the linker is not required to be non-interfering with the non-specific toxicity of the drug, as long as it is cleaved within a period of time short enough to allow the drug to remain localized where it has been activated, or within a period of time short enough to prevent inactivation by any means.

Preferably the prodrugs of the invention are not taken up by the cells, but are cleaved extracellularly by PSA to yield at least 5 picomoles of therapeutic drug per minute per 200 picomoles of PSA. Preferably, the prodrugs yield at least 10 picomoles of cleaved drug per minute per 200 picomoles of PSA. Most preferably, at least 15 picomoles of cleaved drug per minute per 200 picomoles of PSA are produced.

Preferably, the prodrugs of the invention are cleaved by extracellular proteases other than PSA to yield not more than 4.0 picomoles of cleaved therapeutic drug per minute per 200 picomoles of purified extracellular non-PSA proteases. More preferably, the prodrugs are cleaved to yield not more than 2.0 picomoles of cleaved drug per minute per 200 picomoles of purified extracellular non-PSA enzyme. Most preferably, not more than 2.0 picomoles per minute of prodrug are cleaved per 200 picomoles of purified extracellular non-PSA enzyme.

Preferably, the prodrugs of the invention yield at most 2.0 picomoles per minute of cleaved therapeutic drug in human serum. More preferably, the prodrugs yield at most 1.75 picomoles per minute of cleaved drug in human serum. Most preferably, at most 1.5 picomoles per minute of cleaved drug are yielded by enzymes found in human serum.

Preferably, the prodrugs of the invention are cleaved by intracellular proteases other than PSA to yield not more than 35 picomoles of cleaved drug per minute per 200 picomoles of purified intracellular protease. More preferably, the prodrugs do not yield more than 20 picomoles of cleaved drug. Most preferably, not more than 5 picomoles of cleaved drug are produced upon cleavage by purified intracellular proteases other than PSA. While not wishing to be bound by any particular theory, it is believed that essentially no pathogenic effects arise from cleavage of the peptides of the compositions of the invention through intracellular proteases, and that these proteases do not play a significant role in the activation of the therapeutic drugs of the invention.

The prodrugs of the invention may also comprise groups which provide solubility to the prodrug as a whole in the solvent in which the prodrug is to be used. Most often the solvent is water. This feature of the invention is important in the event that neither the peptide nor the therapeutic drug is soluble enough to provide overall solubility to the prodrug. These groups include polysaccharides or other polyhydroxylated moieties. For example, dextran, cyclodextrin, starch and derivatives of such groups may be included in the prodrug of the invention.

Sesquiterpene-γ-Lactone Analogs

The invention also features a derivatized sesquiterpene-γ-lactone analog, the derivatization including providing the molecule with a residue substituted with a primary amine. The primary amine can be used to link the derivatized sesquiterpene with various other moieties. Among these are peptides which link to the analog to give prodrugs without significant non-specific toxicity, but enzymatic reactions with PSA affords the toxic drug. These enzymatic reactions can liberate the non-specific toxic thapsigargin derivative, for example by cleavage through hydrolysis or proteolysis, various reactions of the side chains of the peptide, or other reactions which restore the non-specific toxicity of the sesquiterpene-γ-lactone derivative. These reactions can serve to activate the derivatized sesquiterpene locally PSA-producing tissue, and with relative exclusivity to regions in which these enzymatic is reactions take place. For example, if a derivatized sesquiterpene-γ-lactone analog is linked, via a primary amine, to a peptide containing an amino acid sequence which includes a PSA-specific cleavage site, the analog can be released from the peptide selectively in regions where PSA, or other enzymes having the proteolytic activity of PSA, is found. The primary amine can likewise be used to link a derivatizsed sesquiterpene-γ-lactone analog to an antibody which binds an epitope in the target tissue.

Among the sesquiterpene-γ-lactone analogs preferred for use in the present invention are those of the guaianolide, inuchineolide, germacranolide, and eudesmanolide families of sesquiterpene-γ-lactone analogs. These include estafiatin, grossheimin, inuchinenolide, arglabin, thapsigargin and their derivatives, such as thapsigargicin and many others known to those skilled in the art. One of the preferred class of analogs is that based on the thapsigargin structure.

Thapsigargin is a sesquiterpene-γ-lactone having the following molecular structure:

[Chemical structure of thapsigargin showing carbons $C_1$ through $C_{15}$ with substituents $R_1O$, $R_3O$, $AcO$, $OR_2$, $OH$ groups]

wherein $R_1$ and $R_2$ are substituents to be described below, and $R_3$ is an alkanoyl or alkenoyl substituent, preferably angeloyl ($CO-C(CH_3)=CHCH_3$).

Thapsigargin is an effective inhibitor of the $Ca^{2+}$ ion pump proteins of intracellular membranes located in sacroplasmic reticulum (SR) acid endoplasmic reticulum (ER) of skeletal, cardiac, muscle and brain microsomes. As such, it displays a general non-specific toxicity toward many normal host cells. A method of targeting the proliferation independent cytotoxicity of thapsigargin selectively to cancer cells is needed. A number of thapsigargin analogs have been developed which can be coupled to enzymatically susceptible moieties. The analogs of the present invention include thapsigargin analogs that contain primary amines. The primary amines allow the coupling of thapsigargin analogs to appropriate moieties.

Referring to the thapsigargin skeleton, primary amines can be placed in substituent groups pendant from either the C-2 or the C-8 carbon. These positions are substituted with the groups $-OR_1$ and $-OR_2$, respectively in the thapsigargin structure shown above. These substituent groups can comprise primary amine-containing alkanoyl, alkenoyl or arenoyl substituents. Preferably, these substituent groups are represented by the following structures: unsubstituted or alkyl-, aryl-, halo-, alkoxy-, alkenyl-, amido- or amino-substituted $CO-(CH=CH)_{n1}-(CH_2)_{n2}-Ar-NH_2$, $CO-(CH_2)_{n2}-(CH=CH)_{n1}-Ar-NH_2CO-(CH_2)_{n2}-(CH=CH)_{n1}-CO-NH-Ar-NH_2$ and $CO-(CH=CH)_{n1}-(CH_2)_{n2}-CO-NH-Ar-NH_2$ and substituted variations thereof, where n1 and n2 are from 0 to 5, Ar is any substituted or unsubstituted aryl group, and the position of $NH_2$ on Ar can be ortho, meta or para with respect to the position of the remainder of the substituent group.

Preferred substituent groups are 6-(N-[3-amino-4-methylphenyl]-carboxamido)hexanoyl, 4-(N-[3-amino-4-methylphenyl]-carboxamido)butanoyl, 3-(N-[3-amino-4-methylphenyl]-carboxamido)propanoyl, 4-aminobenzoyl, 4-aminocinnamoyl, 3-[4-aminophenyl]propionoyl, 2-[4-aminophenyl]acetyl, and 4-[4-aminophenyl]butanoyl, 4-[4-aminophenyl]pentanoyl, 4-[4-aminophenyl]hexanoyl, 4-[4-aminophenyl]heptanoyl, or 4-[4-aminophenyl]octanoyl substituents.

The primary amine-containing thapsigargin analogs as generally outlined above are synthesized by removing the 8-O-butanoyl group by triethylamine catalyzed methanolysis of thapsigargin. Attachment of anhydrides of dicarboxylic acids of various lengths affords analogs in which the acyl group attached to a 0-8 end in a free carboxylic acid. A dicyclohexylcarbodiimide (DCCI) promoted coupling of 2,4-diaminoarene to the carboxylic acid analogs yield primary aromatic amine-containing thapsigargin analogs. The primary amine is a potential coupling point for a number of moieties, including the peptide sequence of the invention, via the carboxyl terminus of the peptide.

The primary amine-containing thapsigargin analogs of the invention have non-specific toxicity toward cells. This toxicity is measured as the concentration of analog needed to kill 50% of clonogenic cells ($LC_{50}$). The $LC_{50}$ of the analogs of the invention is desirably at most 20 µM, preferably at most 5 µM, and more preferably at most 500 nM of analog.

The primary amine-containing thapsigargin analogs of the invention have endoplasmic reticulum $Ca^{2+}$-ATPase inhibitory activity. This activity is measured as the concentration of analog needed to inhibit 50% of this ATPase ($IC_{50}$). The $IC_{50}$ of the analogs of the invention is desirably at most 500 nM, preferably at most 200 nM, and more preferably at most 50 nM of analog.

A preferred thapsigargin molecule is 8-O-(12-[L-leucinoylamino]dodecanoyl)-8-O-debutanoylthapsigargin (L12ADT).

Methods of Treatment Using Prodrugs

The invention also provides methods of treating PSA-producing cell proliferative disorders of the invention with the prodrugs of the invention.

The prodrugs of the invention and/or analogs or derivatives thereof can be administered to any host, including a human or non-human animal, in an amount effective to treat a disorder.

The prodrugs of the invention can be administered parenterally by injection or by gradual infusion over time. The prodrugs can be administered intravenously, intraperitoneally, intramuscularly, subcutaneously, intracavity, or transdermally. Preferred methods for delivery of the prodrug include intravenous or subcutaneous administration. Other methods of administration will be known to those skilled in the art.

Preparations for parenteral administration of a prodrug of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases, and the like.

The term "cell-proliferative disorder" denotes malignant as well as non-malignant cell populations which often appear to differ from the surrounding tissue both morphologically and genotypically. Malignant cells (i.e. cancer) develop as a result of a multistep process. The PSA-specific prodrugs of the invention are useful in treating malignancies of the various organ systems. Essentially, any disorder which is etiologically linked to PSA expression could be considered susceptible to treatment with a PSA-specific prodrug. One such disorder is a malignant cell proliferative disorder, for example. The term "therapeutically effective amount" as used herein for treatment of cell proliferative disorders refers to the amount of prodrug sufficient to cause a reduction in the number of unwanted cells. The term "therapeutically effective" therefore includes the amount of prodrug sufficient to prevent, and preferably reduce by at least 25%, and more preferably to reduce by 90%, the number of unwanted cells. The dosage ranges for the administration of prodrug are those large enough to produce the desired effect. Generally the dosage will vary with age, condition, sex, and extent of the disorder in the subject, and can be determined by one skilled in the art. The dosage can be adjusted by the individual physician in the event of any contraindications. In any event, the effectiveness of treatment can be determined by monitoring tumor ablation. For non-malignant conditions such as benign prostatic hyperplasia the effectiveness of therapy can be monitored clinically by decrease in the size of the prostate on digital rectal exam. In addition, effectiveness can also be measured by evaluating urinary parameters such as voiding frequency, urgency and number of episodes of urination at night (i.e. nocturia).

Method of Producing Prodrugs

The invention, in another aspect, provides a method of producing the prodrugs of the invention. This method involves linking a therapeutically active drug to a peptide of the invention. After the drug and peptide are linked to produce a therapeutic prodrug composition, the non-specific toxicity of the drug is substantially inhibited. In certain embodiments, the peptide is linked directly to the drug. In other embodiments, the peptide is indirectly linked to the drug, the linkage occurring through a linker. In each case the carboxy terminus of the peptide is used for linking. The therapeutic drug contains a primary amine group to facilitate the formation of an amide bond with the peptide. Many acceptable methods of coupling carboxyl and amino groups to form amide bonds are known to those of skill in the art.

This bond is cleaved by PSA, releasing the therapeutic drug. Suitable linkers include any chemical group which contain a primary amine. The linkers for use in the present invention include amino acids, primary amine-containing alkyl, alkenyl or arenyl groups.

The connection between the linker and the therapeutic drug may be of any type known in the art, preferably covalent bonding. The linker group may remain attached to the therapeutic drug if its attachment does not significantly reduce the non-specific toxicity of the drug. In certain embodiments, the linker is a cleavable linker, which may be cleaved either by an external agent, or it may be a self-cleaving linker. External agents which may effect cleavage of the linker include enzymes, proteins, organic or inorganic reagents, protons and any other agents which do not affect the non-specific toxicity of the drug or prodrug.

In certain embodiments, the linker comprises an amino acid sequence. The sequence may be of any length, but is preferably between 1 and 10 amino acids, most preferably between 1 and 5 amino acids in length. Preferred amino acids are leucine, histidine, or amino acid sequences containing these amino acids, especially at their amino termini, although conservative variations of these amino acids may also be utilized.

Other groups may be added to the prodrugs of the invention, including those which render the prodrug soluble in water. These groups include polysaccharides or other polyhydroxylated moieties. For example, dextran, cyclodexhin and starch may be included in the prodrug of the invention.

Method of Screening Tissue

In another aspect the invention provides a method of detecting PSA-producing tissue using the peptides of the invention, as described above. The method is carried out by contacting a detectably labeled peptide of the invention with target tissue for a period of time sufficient to allow PSA to cleave the peptide and release the detectable label. The detectable label is then detected. The level of detection is then compared to that of a control sample not contacted with the target tissue. Many varieties of detectable label are available, including optically based labels, such as chromophoric, chemiluminescent, fluorescent or phosphorescent labels, and radioactive labels, such as alpha, beta or gamma emitting labels. Examples of fluorescent labels include amine-containing coumarins such as 7-amino-4-methylcoumarin, 7-amino-4-trifluoromethyl, and other amine-containing fluorophores such as 6-aminoquinoline, and rhodamines, including rhodamine. Examples of radioactive labels include beta emitters such as $^3H$, $^{14}C$ and $^{125}I$. Examples of chromophoric labels (those that have characteristic absorption spectra) include nitroaromatic compounds such as p-nitroaniline. Examples of chemiluminescent labels include luciferins such as 6-amino-6-deoxyluciferin.

Preferably, the choice of detectable label allows for rapid detection and easily interpretable determinations. Detectable labels for use in the invention preferably show clearly detectable differences between detection from the cleaved and uncleaved state.

The invention provides a method for detecting a cell proliferative disorder which comprises contacting a PSA-specific peptide with a cell suspected of having a PSA-production associated disorder and detecting cleavage of the peptide. The peptide reactive with PSA is labeled with a compound which allows detection of cleavage by PSA. For purposes of the invention, a peptide specific for PSA may be used to detect the level of enzymatically active PSA in biological fluids and tissues such as saliva, blood, or urine. Any specimen containing a detectable amount of antigen can be used. The level of PSA in the suspect cell can be compared with the level in a normal cell to determine whether the subject has a PSA-production associated cell proliferative disorder. Preferably the subject is human.

Method of Screening Prodrugs

The invention also provides a method of selecting potential prodrugs for use in the invention. The method generally consists of contacting prodrugs of the invention with PSA-producing tissue and non-PSA producing tissue in a parallel experiment. "PSA-producing tissue" as used herein is tissue that produces at least 1 ng enzymatically active PSA/mL of fluid from tissue, or at least 1 ng of enzymatically active PSA/$10^6$ cells/24 hours from cells. The prodrugs which exert toxic effects in the presence of PSA-producing tissue, but not in the presence of non-PSA producing tissue are suitable for the uses of the invention. In other words, the $LC_{50}$ concentration of the prodrug in the presence of PSA-producing tissue is at least 3 times lower than the $LC_{50}$ concentration of the prodrug in the presence of non-PSA producing tissue, more preferably at least 20 times lower, and most preferably the $LC_{50}$ concentration of the prodrug in the presence of PSA-producing tissue is at least 100 times lower than the $LC_{50}$ concentration of the prodrug in the presence of non-PSA producing tissue.

Method of Determining PSA Activity

The invention also provides a method of determining the activity of PSA. The method generally consists of contacting delectably labeled prodrugs of the invention with samples may come from fluid drawn from PSA-producing tissue, from tissue culture media, from serum, saliva or urine, or any source which contains PSA. The cleavage of peptide which takes place by PSA results in the release of a detectable label, which is subsequently detected. This detection level is compared to the detection level which is found upon performing a parallel experiment in which the PSA-containing sample is a standard solution made up from purified PSA as described, for example, in Christensson, et al., *Eur. J. Biochem.* 194:755-765, (1990). This comparison results in a determination of the activity of the PSA which is present in the sample, given a correction for any differences in PSA concentration which may exist. Such correction may be accomplished directly by adjusting the concentrations of the standard and sample solutions to match each other or by mathematical correction means.

Method of Imaging Tissue

The invention in another aspect, provides a method of imaging soft tissue or bone metastases by providing peptides of the invention linked to lipophilic imaging labels that can be detected by imaging techniques, for example, positron emission tomography (PET). This method is accomplished generally by administering a peptide of the invention linked to a primary amine-containing lipophilic label to a subject having or suspected of having a PSA-producing associated cell proliferative disorder. The peptide is selectively cleaved from the lipophilic imaging label where enzymatically active PSA occurs in the subject (i.e., PSA producing tissues). The lipophilic imaging label is then drawn into the membranes of cells in the vicinity. After a period of time sufficient to allow cleavage of the peptide by PSA, and to allow the uncleaved peptide to be sufficiently cleared from the subject to allow reliable imaging, the subject is imaged. The lipophilic label accumulates in the soft tissue or bone that produces PSA, and allows a diagnosis of the subject. Suitable labels for PET scanning are radionuclides such as $^{18}F$, $^{11}C$, $^{13}N$ and $^{15}O$, and any other positron emitters known in the art. Lipophilicity can be engineered into the label by introducing the label into lipophilic fragments or moieties known to those in the art, by methods known to those skilled in the art.

The invention will be further described in the following examples, which do not limit the scope of the invention described in the claims.

EXAMPLES

The following examples illustrate the preparation and properties of certain embodiments of the invention. The goal of the following experiments was to identify a PSA-cleavable peptide that had improved pharmacological properties when used in a PSA-activated pro-drug.

Example 1

The development of a PSA-activated pro-drug requires advancements on two fronts: 1) the identification of an optimal peptide sequence to serve as a highly active PSA substrate while being stable to cleavage by other proteases in the body and 2) identification of a thapsigargin derivative that could be chemically coupled to a PSA-substrate peptide, yet retain all the activity of the parent thapsigargin after it was released from the prodrug by PSA activity. These combined efforts resulted in identification of an initial PSA-activated pro-drug which was identified using strategies and systematic screenings that are described in detail elsewhere (see, for example, U.S. Pat. No. 6,410,514). This prodrug contained the peptide sequence Mu-His-Ser-Ser-Lys-Leu-Gln (Mu-HSSKLQ) (SEQ ID NO: 6). This peptide was initially coupled to a fluorophore, 7-amino-4-methyl coumarin to generate the fluorescent PSA substrate Mu-HSSKLQ-AMC (SEQ ID NO: 7). This substrate was then used to determine enzyme kinetics of PSA hydrolysis. Subsequently this peptide was coupled to the L12ADT active drug to generate the prodrug Mu-HSSKLQ//L12ADT (SEQ ID NO: 4) (where // indicates site of PSA cleavage).

Subsequently, a series of studies was initiated to identify a more optimal PSA cleavable peptide. The first study involved synthesis of a series of putative PSA substrates based on the starting sequence GSSKLQ (SEQ ID NO: 8). In brief, this technology involved synthesis of small amount of fluorescent peptide onto cellulose membrane. Addition of PSA to the cellulose membrane containing well resulted in release of fluorescent tag over time. Release rate was dependent on affinity of peptide for PSA. At defined time points, aliquots were removed and tested for total fluorescence in separate plate. The assay allowed for measurement of hydrolysis over 4 time points. From this data a hydrolysis rate was determined for each peptide as summarized below in Tables 1 and 2.

TABLE 1

Hydrolysis of selected putative PSA peptides (SEQ ID NOS 9-28, respectively, in order of appearance) by PSA(10 µg/ml)

| Sequence # | Substrate Sequence | | | | | | P-1 | Relative Hydrolysis Rate |
| --- | --- | --- | --- | --- | --- | --- | --- | --- |
| | P6 | P5 | P4 | P3 | P2 | P1 | | |
| 1P | G | S | S | K | L | Q | F | 278.7 |
| 2P | G | A | S | K | L | Q | L | 278.4 |
| 3P | G | S | A | K | L | Q | L | 207.2 |
| 4P | G | S | S | K | L | Q | R | 131.4 |
| 5P | G | s | S | K | L | Q | L | 104.1 |
| 6P | G | S | s | K | L | Q | L | 103.8 |
| 7P | G | S | S | K | L | Q | L | 100.0 |
| 8P | G | S | S | K | L | Q | G | 61.7 |
| 9P | G | S | S | K | L | Q | A | 61.3 |
| 10P | G | S | S | K | L | Q | S | 54.2 |
| 11P | G | S | S | A | L | Q | L | 43.2 |
| 12P | G | S | S | K | L | Q | Q | 42.7 |
| 13P | G | S | S | K | L | Q | T | 38.1 |
| 14P | G | S | S | K | L | Q | H | 36.9 |
| 15P | G | S | S | K | L | A | L | 31.5 |
| 16P | G | S | S | K | L | Q | l | 26.3 |
| 17P | G | S | S | K | L | q | L | 14.2 |
| 18P | G | S | S | K | l | Q | L | 10.7 |
| 19P | G | S | S | K | A | Q | L | 10.3 |
| 20P | G | S | S | k | L | Q | L | 5.0 |

Most preferred peptide sequence indicated in bold lettering.
D-amino acids in lower case type.

In this first set of peptides, hydrolysis of the test peptide GSSKLQ (SEQ ID NO: 8) was compared to a series of peptides modified in various positions. One type of analysis involved an "alanine scan" in which each position of the peptide was replaced by alanine in an attempt to reveal which amino acids are most critical for PSA activity. This scan revealed that the lysine (K) in P3, the leucine (L) in P2 and glutamine (Q) in P1 position were important factors mediating PSA hydrolysis. In contrast, the serines in positions P4 and P5 could be replaced resulting in enhanced PSA hydrolysis.

A second type of analysis involved substitution of D-amino acids for native L-amino acids in the peptide. This type of analysis is performed to identify amino acids that could be changed to D-configuration in an attempt to make a peptide that is more stable to non-specific hydrolysis by serum proteases. This analysis revealed that D-amino acid substitution in positions P-1, and P1-P3 resulted in significant reduction in PSA hydrolysis whereas D-amino acid substitution could be tolerated in positions P4 and P5 of the peptide.

In the next set of studies a series of peptides were synthesized, some of which were based on substitutions in the test GSSKLQ (SEQ ID NO: 8) peptide and some of which were based on rearrangement of the sequences in the test peptide, Table 2.

TABLE 2

Hydrolysis of additional peptides (SEQ ID NOS 29-43, respectively, in order of appearance) by PSA (10 µg/ml)

| Sequence # | Substrate Sequence | | | | | | P-1 | Relative Hydrolysis Rate |
| --- | --- | --- | --- | --- | --- | --- | --- | --- |
| | P6 | P5 | P4 | P3 | P2 | P1 | | |
| 21P | G | S | S | K | Y | Q | L | 256.9 |
| 22P | G | K | S | Q | Y | Q | L | 234.5 |
| 23P | G | K | S | S | Y | Q | L | 196.0 |
| 24P | G | S | S | K | L | H | L | 170.6 |
| 25P | G | S | S | K | Q | Y | L | 123.3 |
| 26P | G | K | S | Q | L | Q | L | 119.0 |
| 27P | G | K | S | S | L | Q | L | 104.0 |
| 28P | G | S | S | K | L | Q | L | 100.0 |
| 29P | G | S | S | S | Y | Q | L | 85.5 |
| 30P | G | S | S | K | Q | H | L | 72.6 |
| 31P | G | S | S | K | L | Y | L | 65.5 |
| 32P | G | S | S | S | L | Q | L | 52.6 |
| 33P | G | K | S | S | Q | Q | L | 52.0 |
| 34P | G | S | S | K | Q | Q | L | 48.2 |
| 35P | G | S | S | S | Q | Q | L | 11.4 |
| | | | | | | | | 7.2 |

Most preferred peptide sequence indicated in bold lettering.

This analysis revealed unexpectedly that the most significant change that augmented PSA activity was the substitution of the amino acid tyrosine (Y) for leucine (L) in the P2 position of the peptide. The results also confirmed the requirement for lysine (K) in either the P3 or P5 position of the peptide.

On the basis of these results a series of putative fluorescent PSA substrates were synthesized by coupling 7-amino-4-methyl coumarin to the C-terminal carboxyl group of the peptides. These peptides were then incubated with PSA (10 µg/ml) and Michaelis Menton kinetic parameters determined using Lineweaver Burke plots, Table 3. In this study, $K_{cat}/K_m$ ratios were calculated in order to rank peptides. Newly synthesized peptides contained an acetyl protecting group (Ac) at the amino terminus, whereas the test peptide contained the protecting group morpholinylcarbonyl (Mu).

TABLE 3

Kinetic parameters of fluorescent PSA peptides (SEQ ID NOS 44-47 and 7, respectively, in order of appearance)

| Peptide Sequence | Km (μM) | $k_{cat}$ (1/s) | $K_{cat}/Km$ ($s^{-1}M^{-1}$) |
|---|---|---|---|
| 1. Ac-GKSQYQ-AMC | 343 | 0.09 | 278 |
| 2. Ac-GSSKYQ-AMC | 500 | 0.113 | 227 |
| 3. Ac-GsAKYQ-AMC | 653 | 0.143 | 218 |
| 4. Ac-GSSKFQ-AMC | 666 | 0.057 | 86 |
| 5. Mu-HSSKLQ-AMC | 470 | 0.011 | 23.6 |

These analyses revealed that peptides containing tyrosine (Y) in the P2 position had approximately equal Kcat/Km ratios that were 10-fold higher than the Mu-HSSKLQ-AMC (SEQ ID NO: 7) test peptide. In each case this increased activity appeared to be due to ~10-fold improvement in the $k_{cat}$ kinetic parameter.

Figure 1B:
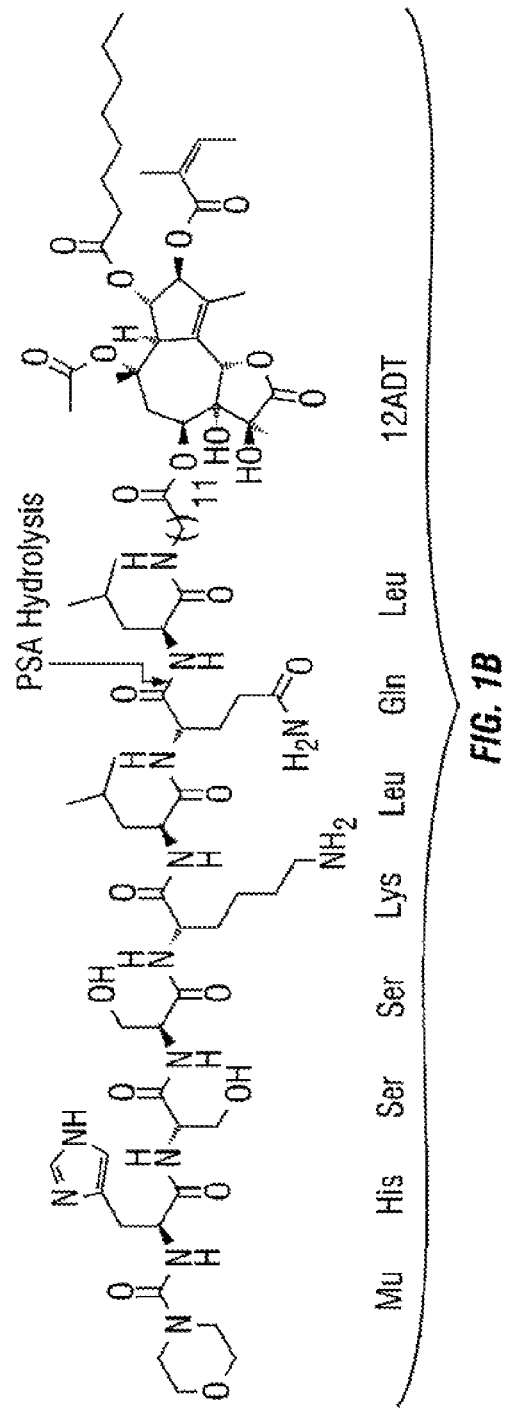
Figure 1C:
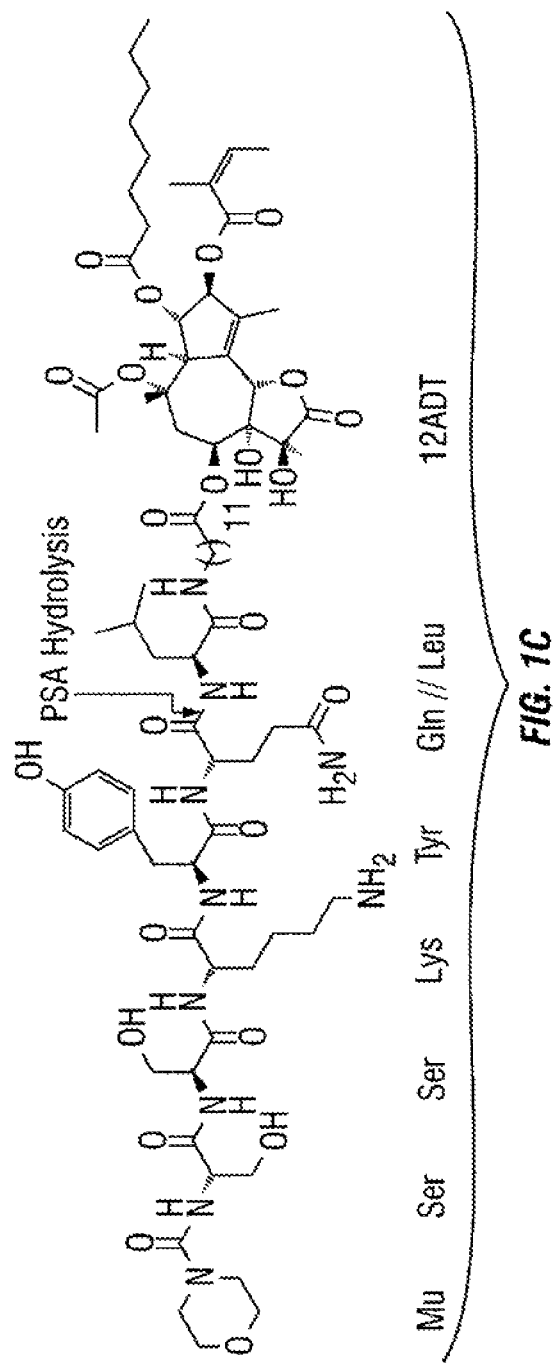

On this basis, the peptide with the sequence GSSKYQ (SEQ ID NO: 48) was selected for further study. For further study, the glycine at the amino terminal end was eliminated from the peptide. In addition, the initial Ac protecting group was replaced by the more water soluble morpholinocarbonyl (Mu) group. Using this rationale, the prodrug Mu-SSKYQ//L12ADT (SEQ ID NO: 5) was synthesized, FIG. 1.

Figure 2:
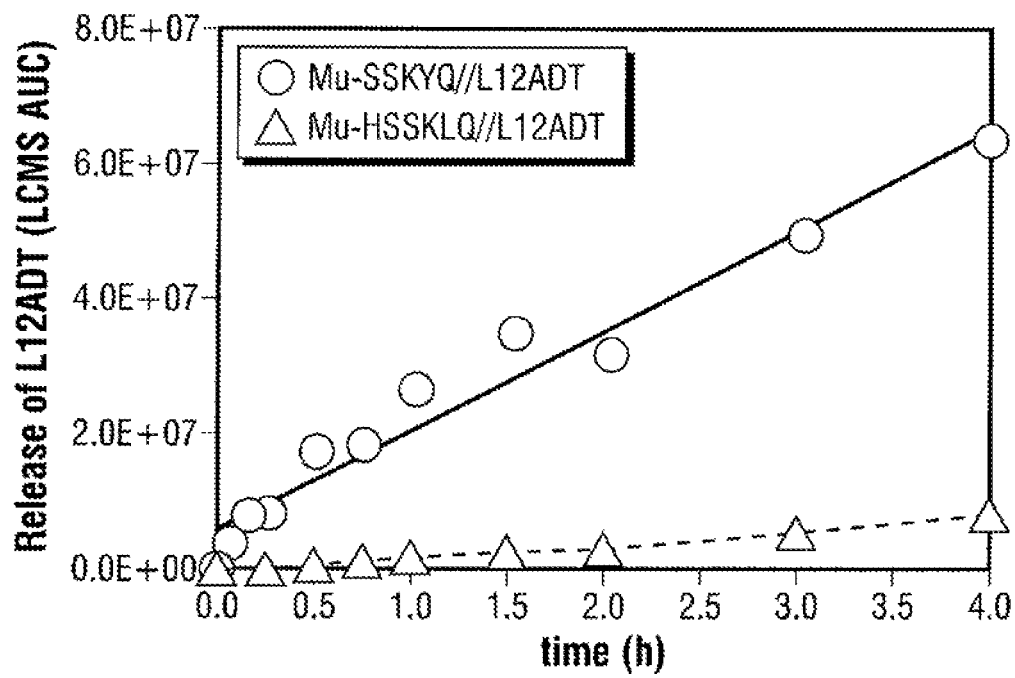
FIG. 2 depicts the hydrolysis of prodrugs (100 µM final concentration) by PSA (10 µg/ml) in PSA buffer (50 mM Tris, 0.1 M NaCl, pH 7.8). Release of product L12ADT was determined by liquid chromatography/mass spectrometric (LC/MS) analysis and calculation of area under the curve (AUC).

Subsequently PSA hydrolysis of the new prodrug Mu-SSKYQ//L12ADT (SEQ ID NO: 5) was compared head to head with the test prodrug Mu-HSSKLQ//L12ADT (SEQ ID NO: 4). Unexpectedly, the new prodrug was hydrolyzed dramatically better than the test peptide, FIG. 2.

Figure 3:
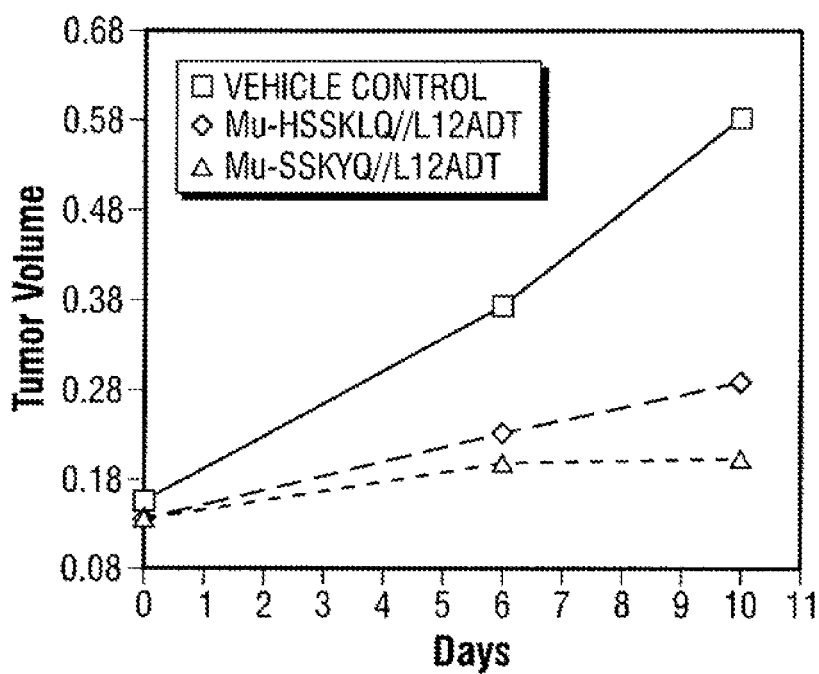
FIG. 3 depicts the antitumor effect of prodrugs compared to vehicle control against CWR22H xenografts following 10 daily injections of 0.1 µmole/dose.

The antitumor efficacy of Mu-SSKYQ//L12ADT (SEQ ID NO: 5) was compared to Mu-HSSKLQ//L12ADT (SEQ ID NO: 4) at equimolar intravenous dose of ~7 mg/kg/day (i.e. 0.1 μmole/dose/day) for 10 consecutive doses, FIG. 3. For these studies we generated a high PSA producing variant of CWR22 through passage in castrate hosts (i.e. CWR22H). This model allows us to assess direct antitumor effects of these prodrugs without concerns that the drugs may lower serum testosterone. In this study, the Mu-HSSKLQ//L12ADT (SEQ ID NO: 4) prodrug had a Tumor Volume/Control Volume (i.e. T/C ratio) of 0.57 after 10 days of therapy whereas the Mu-SSKYQ//L12ADT (SEQ ID NO: 5) had a significantly better T/C ratio of 0.41. In addition, none of the animals in the Vehicle control or the Mu-HSSKLQ//L12ADT (SEQ ID NO: 4) treatment group showed tumor regression, whereas 33% of animals in the Mu-SSKYQ//L12ADT (SEQ ID NO: 5) treated group had regression of tumors from starting size after 10 days of therapy.

Figure 4:
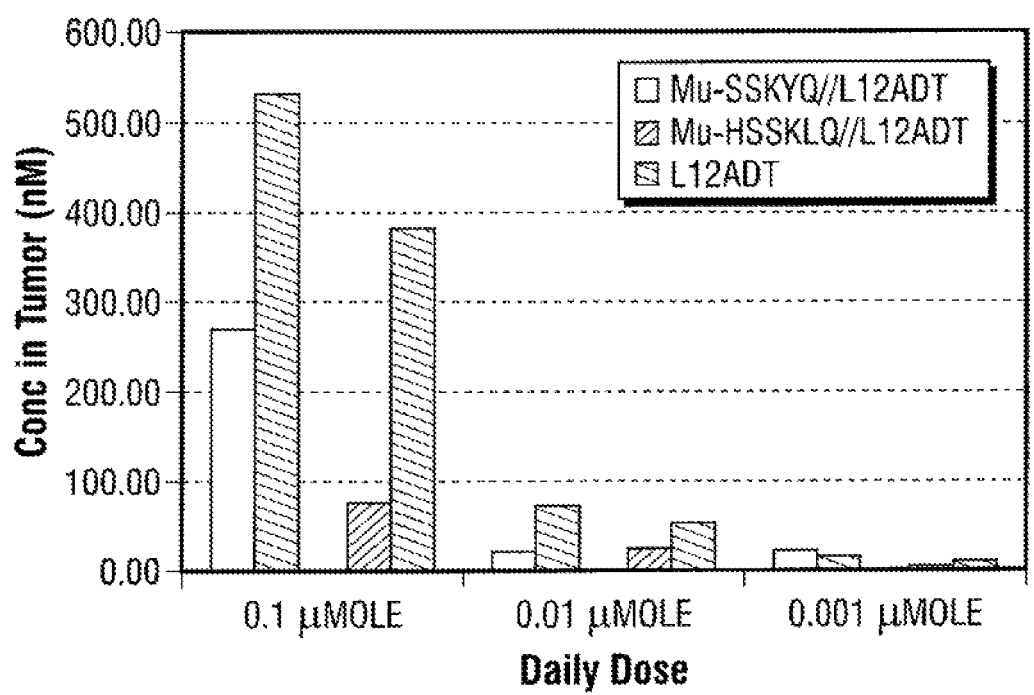
FIG. 4 depicts the trough levels of prodrugs and L12ADT following 10 consecutive intravenous treatments at the indicated dose levels.

In a subsequent study, CWR22H bearing animals were treated for 10 days with either Mu-HSSKLQ//L12ADT (SEQ ID NO: 4) or Mu-SSKYQ//L12ADT (SEQ ID NO: 5) over 3 orders of magnitude of dose levels (i.e. 0.1, 0.01 and 0.001 μmole/dose/day). Twenty four hours after the last dose (i.e. trough), tumors were harvested, homogenized and trough levels of prodrug and free L12ADT determined using LC/MS analysis, FIG. 4.

The disclosed results demonstrate that at each dose level, comparatively higher amounts of the active drug L12ADT are released from the Mu-SSKYQ//L12ADT (SEQ ID NO: 5) prodrug than from the Mu-HSSKLQ//L12ADT (SEQ ID NO: 4) prodrug. These results are consistent with the in vitro biochemical studies showing enhanced cleavage of the Mu-SSKYQ//L12ADT (SEQ ID NO: 5) prodrug by PSA.

In summary the results presented above document that the Mu-SSKYQ//L12ADT (SEQ ID NO: 5) prodrug represents a significant improvement over the previous Mu-HSSKLQ//L12ADT (SEQ ID NO: 4) prodrug in terms of PSA hydrolysis, antitumor efficacy against PSA producing human prostate cancer xenografts and generation of active L12ADT drug within the tumors.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising a prodrug, the prodrug comprising:
   a therapeutically active drug; and
   a peptide comprising
   Gly-Ser-Ala-Lys-Tyr-Gln (SEQ ID NO: 3);
   wherein the peptide is linked to the therapeutically active drug to inhibit the therapeutic activity of the drug, and wherein the therapeutically active drug is cleaved from the peptide upon proteolysis by an enzyme having a proteolytic activity of prostate specific antigen (PSA).

2. The composition of claim 1, wherein the peptide is linked directly to the therapeutic drug.

3. The composition of claim 2, wherein the peptide is linked directly to a primary amine group on the drug.

4. The composition of claim 1, wherein the peptide is linked to the therapeutic drug via a linker.

5. The composition of claim 4, wherein the linker is an amino acid sequence.

6. The composition of claim 5, wherein the linker comprises a leucine residue.

7. The composition of claim 1, wherein the therapeutically active drug inhibits a SERCA pump.

8. The composition of claim 7, wherein the therapeutically active drug is selected from the group of primary amine containing thapsigargins or thapsigargin derivatives.

9. The composition of claim 8, wherein the thapsigargin derivative is 8-O-(12-[L-leucinoylamino]dodecanoyl)-8-O-debutanoylthapsigargin (L12ADT).

10. The composition of claim 1, wherein the therapeutically active drug intercalates into a polynucleotide.

11. The composition of claim 1, wherein the therapeutic drug is a compound belonging to the group of thapsigargins which have been derivatized with a moiety containing a primary amino group and the linker is selected from the group consisting of unsubstituted or alkyl-, aryl-, halo-, alkoxy-, alkenyl-, amido-, or amino-substituted CO—(CH=CH)$_{n1}$—(CH$_2$)$_{n2}$—Ar—NH$_2$, CO—(CH$_2$)$_{n2}$—(CH=CH)$_{n1}$—Ar—NH$_2$, CO—(CH$_2$)$_{n2}$—(CH=CH)$_{n1}$—CO—NH—Ar—NH$_2$ and CO—(CH=CH)$_{n1}$—(CH$_2$)$_{n2}$—CO—NH—Ar—NH$_2$
   wherein n1 and n2 are from 0 to 5, Ar is any substituted or unsubstituted aryl group, and attachment of NH$_2$ to Ar is in a ortho, meta or para position with respect to the remainder of the linker.

12. The composition of claim 1, wherein the therapeutically active drug has an IC$_{50}$ toward ER Ca$^{2+}$-ATPase of at most 500 nM.

13. The composition of claim 12, wherein the therapeutically active drug has an IC$_{50}$ toward ER Ca$^{2+}$-ATPase of at most 50 nM.

14. The composition of claim 1, wherein the therapeutically active drug has an LC$_{50}$ toward PSA-producing tissue of at most 20 μM.

15. The composition of claim 14, wherein the therapeutically active drug has an LC$_{50}$ toward PSA-producing tissue of less than or equal to 2.0 μM.

16. The composition of claim 1, wherein cleavage of the peptide by the enzyme yields at least 5 picomoles of cleaved peptide per minute per 200 picomoles of enzyme.

17. The composition of claim 1, wherein cleavage of the peptide in human serum yields at most 2.0 picomoles of cleaved peptide per minute.

18. The composition of claim 1, further comprising an added substituent which renders the composition water soluble.

19. The composition of claim 18, wherein the added substituent is a polysaccharide.

20. The composition of claim 19, wherein the polysaccharide is selected from the group consisting of modified or unmodified dextran, cyclodextrin and starch.

21. A method of treating a PSA-producing cell proliferative disorder; the method comprising administering the compound of claim 1 in a therapeutically effective amount to a subject having the cell proliferative disorder.

22. The method of claim 21, wherein the disorder is benign.

23. The method of claim 22, wherein the benign disorder is benign prostate hyperplasia.

24. The method of claim 21, wherein the disorder is malignant.

25. The method of claim 24, wherein the malignant disorder is prostate cancer.

26. The method of claim 25, wherein the malignant disorder is breast cancer.

27. The method of claim 21, wherein the therapeutically active drug is the thapsigargin derivative 8-O-(12-[L-leucinoylamino]dodecanoyl)-8-O-debutanoylthapsigargin (L12ADT).

28. The composition of claim 1, wherein the peptide consists of the sequence of Gly-Ser-Ala-Lys-Tyr-Gln (SEQ ID NO: 3).

29. The composition of claim 1, wherein the therapeutically active drug is a derivatized sesquiterpene-γ-lactone analogue.

30. A prodrug comprising:
   thapsigargin or a thapsigargin derivative; and a peptide comprising the sequence of Gly-Ser-Ala-Lys-Tyr-Gln (SEQ ID NO: 3);
   wherein the peptide is linked to the thapsigargin or the thapsigargin derivative to inhibit the therapeutic activity of the drug, and wherein the thapsigargin or the thapsigargin derivative is cleaved from the peptide upon proteolysis by an enzyme having a proteolytic activity of prostate specific antigen (PSA).

31. A prodrug comprising:
   thapsigargin or a thapsigargin derivative; and a peptide consisting of the sequence of Gly-Ser-Ala-Lys-Tyr-Gln (SEQ ID NO: 3);
   wherein the peptide is linked to the thapsigargin or the thapsigargin derivative to inhibit the therapeutic activity of the drug, and wherein the thapsigargin or the thapsigargin derivative is cleaved from the peptide upon proteolysis by an enzyme having a proteolytic activity of prostate specific antigen (PSA).

* * * * *

SEQUENCE LISTING

<160> NUMBER OF SEQ ID NOS: 48

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ser Lys Tyr Gln
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 2

Gly Lys Ser Gln Tyr Gln
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Ser Ala Lys Tyr Gln
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term morpholinocarbonyl
<220> FEATURE:
<221> NAME/KEY: MOD_RES
<222> LOCATION: (7)..(7)
<223> OTHER INFORMATION: 8-O-(12-[L-leucinoylamino]dodecanoyl)-8-O-
      debutanoylthapsigargin

<400> SEQUENCE: 4

His Ser Ser Lys Leu Gln Leu
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term morpholinocarbonyl
<220> FEATURE:
<221> NAME/KEY: MOD_RES
<222> LOCATION: (6)..(6)
<223> OTHER INFORMATION: 8-O-(12-[L-leucinoylamino]dodecanoyl)-8-O-
      debutanoylthapsigargin

<400> SEQUENCE: 5

Ser Ser Lys Tyr Gln Leu
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term morpholinocarbonyl

<400> SEQUENCE: 6

His Ser Ser Lys Leu Gln
1               5
```

```
<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term morpholinocarbonyl
<220> FEATURE:
<223> OTHER INFORMATION: C-term 7-amino-4-methyl coumarin

<400> SEQUENCE: 7

His Ser Ser Lys Leu Gln
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Ser Lys Leu Gln
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ser Ser Lys Leu Gln Phe
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Ala Ser Lys Leu Gln Leu
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ser Ala Lys Leu Gln Leu
1               5

<210> SEQ ID NO 12
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 12

Gly Ser Ser Lys Leu Gln Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ser

<400> SEQUENCE: 13

Gly Ser Ser Lys Leu Gln Leu
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ser

<400> SEQUENCE: 14

Gly Ser Ser Lys Leu Gln Leu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Ser Ser Lys Leu Gln Leu
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ser Ser Lys Leu Gln Gly
1               5

<210> SEQ ID NO 17
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 17

Gly Ser Ser Lys Leu Gln Ala
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ser Ser Lys Leu Gln Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Ser Ser Ala Leu Gln Leu
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ser Ser Lys Leu Gln Gln
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ser Ser Lys Leu Gln Thr
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ser Ser Lys Leu Gln His
1               5
```

```
<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Ser Ser Lys Leu Ala Leu
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Leu

<400> SEQUENCE: 24

Gly Ser Ser Lys Leu Gln Leu
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Gln

<400> SEQUENCE: 25

Gly Ser Ser Lys Leu Gln Leu
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-Leu

<400> SEQUENCE: 26

Gly Ser Ser Lys Leu Gln Leu
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Ser Ser Lys Ala Gln Leu
```

```
<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Lys

<400> SEQUENCE: 28

Gly Ser Ser Lys Leu Gln Leu
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ser Ser Lys Tyr Gln Leu
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Lys Ser Gln Tyr Gln Leu
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Lys Ser Ser Tyr Gln Leu
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Ser Ser Lys Leu His Leu
1               5

<210> SEQ ID NO 33
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ser Ser Lys Gln Tyr Leu
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Lys Ser Gln Leu Gln Leu
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Lys Ser Ser Leu Gln Leu
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Ser Ser Lys Leu Gln Leu
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Ser Ser Ser Tyr Gln Leu
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ser Ser Lys Gln His Leu
```

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Ser Ser Lys Leu Tyr Leu
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Ser Ser Ser Leu Gln Leu
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Lys Ser Ser Gln Gln Leu
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Ser Ser Lys Gln Gln Leu
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Ser Ser Ser Gln Gln Leu
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic

```
        peptide
<220> FEATURE:
<223> OTHER INFORMATION: N-term Ac
<220> FEATURE:
<223> OTHER INFORMATION: C-term 7-amino-4-methyl coumarin

<400> SEQUENCE: 44

Gly Lys Ser Gln Tyr Gln
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term 7-amino-4-methyl coumarin

<400> SEQUENCE: 45

Gly Ser Ser Lys Tyr Gln
1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term 7-amino-4-methyl coumarin
<220> FEATURE:
<221> NAME/KEY: MOD_RES
<222> LOCATION: (2)..(2)
<223> OTHER INFORMATION: D-Ser

<400> SEQUENCE: 46

Gly Ser Ala Lys Tyr Gln
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term 7-amino-4-methyl coumarin

<400> SEQUENCE: 47

Gly Ser Ser Lys Phe Gln
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 48

Gly Ser Ser Lys Tyr Gln
1               5
```